(12) United States Patent
Blake et al.

(10) Patent No.: US 12,290,055 B2
(45) Date of Patent: May 6, 2025

(54) TRANSGENIC BETTA

(71) Applicant: GloFish, LLC, Earth City, MO (US)

(72) Inventors: Alan Blake, Austin, TX (US); Richard Crockett, Wilton, CT (US); Aidas Nasevicius, Tampa, FL (US)

(73) Assignee: GloFish, LLC, Earth City, MO (US)

( * ) Notice: Subject to any disclaimer, the term of this patent is extended or adjusted under 35 U.S.C. 154(b) by 959 days.

(21) Appl. No.: 17/293,415

(22) PCT Filed: Nov. 13, 2019

(86) PCT No.: PCT/US2019/061155
§ 371 (c)(1),
(2) Date: May 12, 2021

(87) PCT Pub. No.: WO2020/102333
PCT Pub. Date: May 22, 2020

(65) Prior Publication Data
US 2022/0022432 A1    Jan. 27, 2022

Related U.S. Application Data

(60) Provisional application No. 62/760,480, filed on Nov. 13, 2018, provisional application No. 62/760,445, filed on Nov. 13, 2018, provisional application No. 62/760,464, filed on Nov. 13, 2018, provisional application No. 62/760,498, filed on Nov. 13, 2018, provisional application No. 62/760,489, filed on Nov. 13, 2018.

(51) Int. Cl.
*A01K 67/0275* (2024.01)
*C12N 15/85* (2006.01)

(52) U.S. Cl.
CPC ...... *A01K 67/0275* (2013.01); *C12N 15/8509* (2013.01); *A01K 2227/40* (2013.01); *A01K 2267/01* (2013.01)

(58) Field of Classification Search
CPC .............. A01K 2227/40; A01K 67/027; A01K 67/0275
See application file for complete search history.

(56) References Cited

U.S. PATENT DOCUMENTS

| | | |
|---|---|---|
| 7,135,613 B1 | 11/2006 | Gong et al. |
| 7,355,095 B2 | 4/2008 | Tsai et al. |
| 7,700,825 B2 | 4/2010 | Blake et al. |
| 7,834,239 B2 | 11/2010 | Gong et al. |
| 8,232,450 B1 | 7/2012 | Blake et al. |
| 8,232,451 B1 | 7/2012 | Blake et al. |
| 8,378,169 B2 | 2/2013 | Gong et al. |
| 8,581,025 B2 | 11/2013 | Blake et al. |
| 9,968,077 B2 | 5/2018 | Blake et al. |
| 10,798,923 B2 | 10/2020 | Blake et al. |
| 2002/0178461 A1 | 11/2002 | Lin |
| 2003/0162292 A1 | 8/2003 | Tsai et al. |
| 2004/0117866 A1 | 6/2004 | Tsai |
| 2004/0143864 A1 | 7/2004 | Gong et al. |
| 2005/0198701 A1 | 9/2005 | Lian et al. |
| 2005/0273874 A1 | 12/2005 | Tsai et al. |
| 2008/0052787 A1 | 2/2008 | Gong et al. |
| 2009/0025645 A1 | 1/2009 | Blake et al. |
| 2009/0035788 A1 | 2/2009 | Griesbeck et al. |
| 2009/0133138 A1 | 5/2009 | Tsai |
| 2009/0255006 A1 | 10/2009 | Dougan et al. |
| 2010/0037330 A1 | 2/2010 | Siripattarappavat et al. |
| 2010/0037331 A1 | 2/2010 | Blake et al. |
| 2010/0050280 A1 | 2/2010 | Blake et al. |
| 2010/0145889 A1 | 6/2010 | Blake et al. |
| 2012/0210453 A1 | 8/2012 | Blake et al. |
| 2012/0317665 A1 | 12/2012 | Blake et al. |
| 2013/0133093 A1 | 5/2013 | Blake et al. |
| 2013/0333060 A1 | 12/2013 | Blake et al. |
| 2014/0033338 A1 | 1/2014 | Blake et al. |
| 2014/0130195 A1 | 5/2014 | Blake et al. |
| 2015/0216148 A1 | 8/2015 | Blake et al. |
| 2015/0216149 A1 | 8/2015 | Blake et al. |
| 2015/0216150 A1 | 8/2015 | Blake et al. |
| 2015/0216151 A1 | 8/2015 | Blake et al. |
| 2016/0128310 A1* | 5/2016 | Blake ................. A01K 67/0275 800/20 |
| 2017/0258057 A1 | 9/2017 | Blake et al. |

(Continued)

FOREIGN PATENT DOCUMENTS

| | | |
|---|---|---|
| CN | 1590548 | 3/2005 |
| CN | 103540611 A | 1/2014 |

(Continued)

OTHER PUBLICATIONS

Zhu Z. et al., Novel gene transfer into the fertilized eggs of gold fish (*Carassius auratus* L. 1758), Institute of Hydrobiology, Academia Sinica, Wuhan, P.R. China (1985).
Du S.J et al., "Growth enhancement in transgenic atlantic salmon by the use of an "All Fish" chimeric growth hormone gene contrust", Bio/Technology, Nature Publishing Group, vol. 10: 176-181 (1992).
Khoo H.W. et al., "Sperm cells as vectors for introducing foreign DNA into ebrafish", Aquaculture, 107, issue 1: 1-19 (1992).
Sin F.Y.T. et al., Gene transer in chinook salmon (*Oncorhynchus tshawytscha*) by electroporating sperm in the presence of pRSV-lacZ DNA, Aquaculture, 117: 57-69 (1993).
Zelenin A.V. et al., "The delivery of foreign genes into fertilized fish eggs using high-velocity microprojectiles", FEBS Lett. 287(1-2): 118-120 (1991).
Szelei J. et al., "Liposome-mediated gene transfer in fish embryos", Transgenic Research 3: 116-119 (1994).
Xu Y. et al., "Fast Skeletal Muscle-Specific Expression of a Zebrafish Myosin Light Chain 2 Gene and Characterization of Its Promoter by Direct Injection into Skeletal Muscle", DNA and Cell Biology, vol. 18: 85-95 (1999).

(Continued)

*Primary Examiner* — Christopher M Babic
*Assistant Examiner* — Jennifer S Spence
(74) *Attorney, Agent, or Firm* — Brown Rudnick LLP; Ryan C. Smith

(57) ABSTRACT

The present invention relates to transgenic ornamental fish, as well as methods of making such fish by germ cell transplantation techniques. Also disclosed are methods of establishing a population of such transgenic fish and methods of providing them to the ornamental fish industry for the purpose of marketing.

21 Claims, No Drawings

(56) References Cited

U.S. PATENT DOCUMENTS

| | | |
|---|---|---|
| 2020/0113159 A1 | 4/2020 | Blake et al. |
| 2020/0396972 A1 | 12/2020 | Blake et al. |
| 2021/0051927 A1 | 2/2021 | Blake et al. |
| 2022/0090126 A1 | 3/2022 | Blake et al. |

FOREIGN PATENT DOCUMENTS

| | | |
|---|---|---|
| CN | 106070063 A | 11/2016 |
| EP | 2166107 | 3/2010 |
| JP | 2004-321173 A | 11/2004 |
| WO | WO 2000/049150 | 8/2000 |
| WO | WO 2008/022208 | 2/2008 |
| WO | WO 2009/148549 | 10/2009 |
| WO | 2018/183728 A1 | 10/2018 |

OTHER PUBLICATIONS

Chourrout D. et al., "High efficiency gene transfer in rainbow trout (*Salmo gairdneri* Rich.) by microinjection into egg cytoplasm", Acuaculture, 51: 143-150 (1986).

Penman D.J. et al., "Factors Affecting Survival and Integration Following Microinjection of Novel DNA into Rainbor Trout Eggs", Aquaculture, 85: 35-50 (1990).

Brem G. et al., Gene Transfer in Tilapia (*Oreochromis nilotics*), Aquaculture 68: 209-219 (1988).

Gross M.L. et al., "Molecular analysis and growth evaluation of northern pike (*Esox lucius*) microinjected with growth hormone genes", Aquaculture, 103: 253-273 (1992).

Devlin R.H. et al., "Extraordinary salmon growth", Scientific Correspondence, Nature, vol. 371: 209-210 (1994).

Tsai H.J. et al., Electroporation of sperm to introduce foreign DNA into the genome of loach (*Misgurnus anguuillicauatus*): Can. J. Fish, Aquat. Sci. 52: 776-787 (1995).

Shagin et al., "GFP-like Proteins as Ubiquitous Metazoan Superfamily: Evolution of Functional Features and Structural Complexity", Molecular Biology and Evolution, vol. 21(5): 841-850 (2004).

C. Walker and G. Streisinger, Freezing Sperm in Zebrafish Book—A guide for the Laboratory Use of Zebrafish (*Danio rerio*) 4th Edition ZFIN: Breeding Zebrafish, University of Oregon (2016).

Draper et al., "A High-Throughput Method for Zebrafish Sperm Cryopreservation and In Vitro Fertilization", Journal of Visualized Experiments, Jove, 29, e1395: 1-5 (2009).

Vick B.M. et al., "Learning the scientific method using GloFish", Zebrafish, vol. 9(4): 226-241 (2012).

International Search Report and Written Opinion for PCT/US2018/025224, mailed Jul. 6, 2018.

International Search Report and Written Opinion for PCT/US2019/013072, mailed Apr. 26, 2019.

International Search Report and Written Opinion for PCT/US2019/061155, mailed Mar. 13, 2020.

International Search Report and Written Opinion for PCT/US2020/013102, mailed Jun. 19, 2020.

Berquand et al., "Analysis of Cytoskeleton-Destabilizing Agents by Optimized Optical Navigation and AFM Force Measurements," *Microscopy Today*, 18:34-37, 2010.

Day et al., "Fluorescent protein tools for studying protein dynamics in living cells: a review," *J Biomed Opt.*, 3(3):031202, 2008.

Finley et al., "Three-color imaging using fluorescent proteins in living zebrafish embryos," *Biotechniques*, 31(1):66-70; 72, 2001.

Franco et al., "Control of initial endothelial spreading by topographic activation of focal adhesion kinase," *Soft Matter.*, 77:313-7324, 2011.

Gong et al., "Development of transgenic fish for ornamental and bioreactor by strong expression of fluorescent proteins in the skeletal muscle," *Biochem. Bio phys. Res. Commun.*, 308(1):58-63, 2003.

Gong et al., "Green fluorescent protein (GFP) transgenic fish and their applications," *Genetica*, 111(1-3):213-25, 2001.

Ju et al., "Recapitulation of fast skeletal muscle development in zebrafish by transgenic expression of GFP under the mylz2 promoter," *Dev Dyn.*, 227(1):14-26, 2003.

Laranjeira et al., "Glial cells in the mouse enteric nervous system can undergo neurogenesis in response to injury," *J Clin Invest.*, 121(9):3412-24, 2011.

Liu et al., "Development of expression vectors for transgenic fish," *Biotechnology*, 8: 1268-1272, 1990.

Liu et al., "Isolation and characterization of beta-actin gene of carp (*Cyprinus carpio* )," *DNA Seq.*, 1(2):125-36, 1990.

Martynov et al., "Alternative cyclization in GFP-like proteins family," *The Journal of Biological Chemistry*, 276(24):21012-21016, 2001.

Nowotschin et al., "Live-imaging fluorescent proteins in mouse embryos: multi-dimensional, multi-spectral perspectives," *Trends in Biotechnology*, 27(5):266-276, 2009.

Parichy et al., "Zebrafish hybrids suggest genetic mechanisms for pigment pattern diversification in *Danio*," *Dev. Genes Evol.*, 211:319-328, 2001.

Shcherbo et al., "Bright far-red fluorescent protein for whole-body imaging," *Nature Methods*, 4(9):741-746, 2007.

Shkrob et al., "Far-red fluorescent proteins evolved from a blue chromoprotein from *Actinia equina*," *Biochem. J.*, 392:649-654, 2005.

Stewart, "Go with the glow: fluorescent proteins to light transgenic organisms," *Trends Biotechnol.*, 24(4):155-62, 2006.

Subach et al., "Conversion of red fluorescent protein into a bright blue probe," *Chemistry & Biology*, 15:1116-1124, 2008.

Urbani, "Multi-Color approach to track Salmonella during infection," *University of Basel, Master's Thesis*, pp. 1-35, Oct. 15, 2009.

Wan et al., "Generation of two-color transgenic zebrafish using the green and red fluorescent protein reporter genes gfp and rfp," *Mar Biotechnol (NY)*, 4(2)146-54, 2002.

Zhu et al., "Regulation of the lmo2 promoter during hematopoietic and vascular development in zebrafish," *Dev. Biol.*, 281(2):256-269, 2005.

Zhu et al., "Use of the DsRed fluorescent reporter in zebrafish," *Methods Cell. Biol.*, 76:3-12, 2004.

Design U.S. Appl. No. 29/501,874 entitled "Bright Red Fluorescent Tetra" by Alan Blake et al., filed Sep. 9, 2014.

Design U.S. Appl. No. 29/501,878 entitled "Bright Blue Fluorescent Tetra" by Alan Blake et al., filed Sep. 9, 2014.

Fenner, The Rainbow, Redfin and Albino Minnow sharks *Epalzeorhynchos munense* and *E. frenatum*, The Conscientious Aquarist, WetWebMedia.com, retrieved by Wikipedia on Aug. 17, 2007 (Year: 2007).

Wikipedia description of rainbow shark (2022) (Year: 2022).

\* cited by examiner

TRANSGENIC BETTA

CROSS REFERENCE TO RELATED APPLICATIONS

This application is a National Stage application of PCT/US2019/061155, filed Nov. 13, 2019, which claims priority to U.S. Patent Application No. 62/760,445, filed Nov. 13, 2018 and entitled Transgenic Green Betta, U.S. Patent Application No. 62/760,464, filed Nov. 13, 2018 and entitled Transgenic Orange Betta, U.S. Patent Application No. 62/760,480, filed Nov. 13, 2018 and entitled Transgenic Red Betta, U.S. Patent Application No. 62/760,489, filed Nov. 13, 2018 and entitled Transgenic Purple Betta, and U.S. Patent Application No. 62/760,498, filed Nov. 13, 2018 and entitled Transgenic Blue Betta, the disclosures of which are hereby incorporated by reference herein in their entirety. To the extent appropriate, a claim of priority is made to each of the above disclosed applications.

FIELD OF THE INVENTION

This invention relates to transgenic fish. Specifically, the invention relates to orange transgenic betta. Specifically, the invention relates to purple transgenic betta. Specifically, the invention relates to blue transgenic betta. Specifically, the invention relates to green transgenic betta. Specifically, the invention relates to red transgenic betta. Specifically, the invention relates to pink transgenic betta.

INTRODUCTION

Transgenic technology involves the transfer of a foreign gene into a host organism enabling the host to acquire a new and inheritable trait. Transgenic technology has many potential applications. For example, it can be used to introduce a transgene into a fish in order to create new varieties of fish. There are many ways of introducing a foreign gene into fish, including: microinjection (e.g., Zhu et al., 1985; Du et al., 1992), electroporation (Powers et al., 1992), sperm-mediated gene transfer (Khoo et al., 1992; Sin et al., 1993), gene bombardment or gene gun (Zelenin et al., 1991), liposome-mediated gene transfer (Szelei et al., 1994), and the direct injection of DNA into muscle tissue (Xu et al., 1999). The first transgenic fish report was published by Zhu et al., (1985) using a chimeric gene construct consisting of a mouse metallothionein gene promoter and a human growth hormone gene. Most of the early transgenic fish studies have concentrated on growth hormone gene transfer with an aim of generating fast growing fish. While a majority of early attempts used heterologous growth hormone genes and promoters and failed to produce these fish (e.g. Chourrout et al., 1986; Penman et al., 1990; Brem et al., 1988; Gross et al., 1992), enhanced growth of transgenic fish has been demonstrated in several fish species including Atlantic salmon, several species of Pacific salmons, and loach (e.g. Du et al., 1992; Delvin et al., 1994, 1995; Tsai et al., 1995).

The Siamese fighting fish (Betta splendens), also sometimes colloquially known as the betta, is a species in the gourami family, which is popular as an aquarium fish. Species assigned to Betta splendens display a broad diversity of body shapes and coloration. The genus is well known among aquarists. Bettas can be territorial fish and are prone to high levels of aggression towards each other. Two males in proximity will almost always attack each other, if they do not have the ability to escape this will usually result in the death of one or both of the fish. Female bettas can also become territorial towards each other if they are housed in too small an aquarium.

Wild fish exhibit strong colors only when agitated. Breeders have been able to make this coloration permanent, and a wide variety of hues breed true. Colors available to the aquarist include red, orange, yellow, blue, steel blue, turquoise/green, black, pastel, white ("opaque" white, not to be confused with albino) and multi-colored fish.

Bettas are found in many different colors due to different layers of pigmentation in their skin. The layers (from furthest within to the outer layer) consists of red, yellow, black, iridescent (blue and green), and metallic (not a color of its own, but reacts with the other colors to change how they are perceived). Any combination of these layers can be present, leading to a wide variety of colors.

However, for the ornamental fish industry, the bold colors can be enhanced or novel colors can be introduced to provide a more efficient display of the various colors. The availability of such Bettas having modified pigmentation by transgenesis with fluorescent proteins would result in better products for the ornamental fish industry due to better visualization of the various colors.

Many fluorescent proteins are known in the art and have been used to investigate various cellular processes, including fluorescent proteins exhibiting various green, red, pink, yellow, orange, blue, or purple colors. Although transgenic experiments involving fluorescent proteins have provided new markers and reporters for transgenesis, progress in the field of developing and producing Bettas that express such proteins has been limited.

Transgenic Betta

In certain embodiments, the present disclosure concerns making transgenic fluorescent fish and providing such fish to the ornamental fish industry.

In some embodiments, transgenic fish or methods of making transgenic fish are provided. In certain aspects, the transgenic fish are fertile, transgenic, fluorescent fish. In a particular embodiment, the fish for use with the disclosed constructs and methods is the Betta. Betta skin color is determined by pigment cells in the skin, which contain pigment granules called melanosomes (black or brown color), xanthosomes (yellow color), erythrosomes (orange or red color), or iridosomes (iridescent colors, including white color). The number, size, and density of the pigment granules per pigment cell influence the color of the fish skin.

In certain specific embodiments, there are provided transgenic Betta or progeny thereof comprising specific transgenic integration events, referred to herein as transformation events. These fish are of particular interest because, for example, they embody an aesthetically pleasing green color. Transgenic fish comprising these specific transgenic events may be homozygous or heterozygous (including, for example, hemizygous) for the transformation event. Homozygous fish bred with fish lacking a transformation event will in nearly all cases produce 100% heterozygous offspring. Germ cells, eggs, sperm, and embryos comprising these specific transgenic events are also included as part of the invention.

In one such embodiment regarding a specific transgenic integration event, a green transgenic Betta or progeny thereof is provided comprising chromosomally integrated transgenes, wherein the Betta comprises the "Green Betta 1 transformation event," cryopreserved testes comprising the Green Betta 1 transformation event having been deposited at the ATCC under Provisional Accession Number PTA-126548. The chromosomally integrated transgenes may be present on one integrated expression cassette or two or more integrated expression cassettes. In certain aspects, such a transgenic Betta is a fertile, transgenic Betta. Such a transgenic Betta may be homozygous or heterozygous (including, for example, hemizygous) for the transgenes or integrated expression cassette(s).

Also disclosed are methods of providing a transgenic Betta comprising the Green Betta 1 transformation event to the ornamental fish market. In some embodiments, the method comprises obtaining a transgenic Betta or progeny thereof comprising chromosomally integrated transgenes, wherein the Betta comprises the "Green Betta 1 transformation event," cryopreserved testes comprising the Green Betta 1 transformation event being deposited at the ATCC under Provisional Accession Number PTA-126548, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Betta are provided comprising: (a) obtaining a Betta that exhibits fluorescence and comprises one or more chromosomally integrated transgenes or expression cassettes, wherein the Betta comprises the "Green Betta 1 transformation event," cryopreserved testes comprising the Green Betta 1 transformation event being deposited at the ATCC under Provisional Accession Number PTA-126548; and (b) breeding the obtained Betta with a second Betta to provide a transgenic Betta comprising the Green Betta 1 transformation event. The second Betta may be a transgenic or non-transgenic Betta.

In further embodiments, also provided are methods of producing a transgenic organism, the method comprising using cryopreserved testes comprising the Green Betta 1 transformation, such cryopreserved testes deposited at the ATCC under Provisional Accession Number PTA-126548, to produce transgenic offspring. Such offspring may be, for example, a Betta, a species of the Betta splendens family, a fish species or genus related to Betta, or another fish species or genus. In some aspects, the fish may be produced using in vitro fertilization.

In another such embodiment regarding a specific transgenic integration event, a an orange transgenic Betta or progeny thereof is provided comprising chromosomally integrated transgenes, wherein the Betta comprises the "Orange Betta 1 transformation event," cryopreserved testes comprising the Orange Betta 1 transformation event having been deposited at the ATCC under Provisional Accession Number PTA-126549. The chromosomally integrated transgenes may be present on one integrated expression cassette or two or more integrated expression cassettes. In certain aspects, such a transgenic Betta is a fertile, transgenic Betta. Such a transgenic Betta may be homozygous or heterozygous (including, for example, hemizygous) for the transgenes or integrated expression cassette(s).

Also disclosed are methods of providing a transgenic Betta comprising the Orange Betta 1 transformation event to the ornamental fish market. In some embodiments, the method comprises obtaining a transgenic Betta or progeny thereof comprising chromosomally integrated transgenes, wherein the Betta comprises the "Orange Betta 1 transformation event," cryopreserved testes comprising the Orange Betta 1 transformation event being deposited at the ATCC under Provisional Accession Number PTA-126549, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Betta are provided comprising: (a) obtaining a Betta that exhibits fluorescence and comprises one or more chromosomally integrated transgenes or expression cassettes, wherein the Betta comprises the "Orange Betta 1 transformation event," cryopreserved testes comprising the Orange Betta 1 transformation event being deposited at the ATCC under Provisional Accession Number PTA-126549; and (b) breeding the obtained Betta with a second Betta to provide a transgenic Betta comprising the Orange Betta 1 transformation event. The second Betta may be a transgenic or non-transgenic Betta.

In further embodiments, also provided are methods of producing a transgenic organism, the method comprising using cryopreserved testes comprising the Orange Betta 1 transformation, such cryopreserved testes deposited at the ATCC under Provisional Accession Number PTA-126549, to produce transgenic offspring. Such offspring may be, for example, a Betta, a species of the Betta splendens family, a fish species or genus related to Betta, or another fish species or genus. In some aspects, the fish may be produced using in vitro fertilization.

In another such embodiment regarding a specific transgenic integration event, a red transgenic Betta or progeny thereof is provided comprising chromosomally integrated transgenes, wherein the Betta comprises the "Red Betta 1 transformation event," cryopreserved testes comprising the Red Betta 1 transformation event having been deposited at the ATCC. The chromosomally integrated transgenes may be present on one integrated expression cassette or two or more integrated expression cassettes. In certain aspects, such a transgenic Betta is a fertile, transgenic Betta. Such a transgenic Betta may be homozygous or heterozygous (including, for example, hemizygous) for the transgenes or integrated expression cassette(s).

Also disclosed are methods of providing a transgenic Betta comprising the Red Betta 1 transformation event to the ornamental fish market. In some embodiments, the method comprises obtaining a transgenic Betta or progeny thereof comprising chromosomally integrated transgenes, wherein the Betta comprises the "Red Betta 1 transformation event," cryopreserved testes comprising the Red Betta 1 transformation event having been deposited at the ATCC, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Betta are provided comprising: (a) obtaining a Betta that exhibits fluorescence and comprises one or more chromosomally integrated transgenes or expression cassettes, wherein the Betta comprises the "Red Betta 1 transformation event," cryopreserved testes comprising the Red Betta 1 transformation event having been deposited at the ATCC; and (b) breeding the obtained Betta with a second Betta to provide a transgenic Betta comprising the Red Betta 1 transformation event. The second Betta may be a transgenic or non-transgenic Betta.

In further embodiments, also provided are methods of producing a transgenic organism, the method comprising using cryopreserved testes comprising the Red Betta 1 transformation, such cryopreserved testes having been deposited at the ATCC, to produce transgenic offspring. Such offspring may be, for example, a Betta, a species of the Betta splendens family, a fish species or genus related to Betta, or another fish species or genus. In some aspects, the fish may be produced using in vitro fertilization.

In another embodiment regarding a specific transgenic integration event, a purple transgenic Betta or progeny thereof is provided comprising chromosomally integrated transgenes, wherein the Betta comprises the "Purple Betta 1 transformation event," cryopreserved testes comprising the Purple Betta 1 transformation event having been deposited at the ATCC. The chromosomally integrated transgenes may be present on one integrated expression cassette or two or more integrated expression cassettes. In certain aspects, such a transgenic Betta is a fertile, transgenic Betta. Such a transgenic Betta may be homozygous or heterozygous (including, for example, hemizygous) for the transgenes or integrated expression cassette(s).

Also disclosed are methods of providing a transgenic Betta comprising the Purple Betta 1 transformation event to the ornamental fish market. In some embodiments, the method comprises obtaining a transgenic Betta or progeny thereof comprising chromosomally integrated transgenes, wherein the Betta comprises the "Purple Betta 1 transformation event," cryopreserved testes comprising the Purple Betta 1 transformation event being deposited at the ATCC, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Betta are provided comprising: (a) obtaining a Betta that exhibits fluorescence and comprises one or more chromosomally integrated transgenes or expression cassettes, wherein the Betta comprises the "Purple Betta 1 transformation event," cryopreserved testes comprising the Purple Betta 1 transformation event being deposited at the ATCC; and (b) breeding the obtained Betta with a second Betta to provide a transgenic Betta comprising the Purple Betta 1 transformation event. The second Betta may be a transgenic or non-transgenic Betta.

In further embodiments, also provided are methods of producing a transgenic organism, the method comprising using cryopreserved testes comprising the Purple Betta 1 transformation, such cryopreserved testes deposited at the ATCC, to produce transgenic offspring. Such offspring may be, for example, a Betta, a species of the Betta splendens family, a fish species or genus related to Betta, or another fish species or genus. In some aspects, the fish may be produced using in vitro fertilization.

In another embodiment regarding a specific transgenic integration event, a blue transgenic Betta or progeny thereof is provided comprising chromosomally integrated transgenes, wherein the Betta comprises the "Blue Betta 1 transformation event," cryopreserved testes comprising the Blue Betta 1 transformation event having been deposited at the ATCC. The chromosomally integrated transgenes may be present on one integrated expression cassette or two or more integrated expression cassettes. In certain aspects, such a transgenic Betta is a fertile, transgenic Betta. Such a transgenic Betta may be homozygous or heterozygous (including, for example, hemizygous) for the transgenes or integrated expression cassette(s).

Also disclosed are methods of providing a transgenic Betta comprising the Blue Betta 1 transformation event to the ornamental fish market. In some embodiments, the method comprises obtaining a transgenic Betta or progeny thereof comprising chromosomally integrated transgenes, wherein the Betta comprises the "Blue Betta 1 transformation event," cryopreserved testes comprising the Blue Betta 1 transformation event being deposited at the ATCC, and distributing the fish to the ornamental fish market. Such fish may be distributed by a grower to a commercial distributor, or such fish may be distributed by a grower or a commercial distributor to a retailer such as, for example, a multi-product retailer having an ornamental fish department.

In some aspects, methods of producing a transgenic Betta are provided comprising: (a) obtaining a Betta that exhibits fluorescence and comprises one or more chromosomally integrated transgenes or expression cassettes, wherein the Betta comprises the "Blue Betta 1 transformation event," cryopreserved testes comprising the Blue Betta 1 transformation event being deposited at the ATCC; and (b) breeding the obtained Betta with a second Betta to provide a transgenic Betta comprising the Blue Betta 1 transformation event. The second Betta may be a transgenic or non-transgenic Betta.

In further embodiments, also provided are methods of producing a transgenic organism, the method comprising using cryopreserved testes comprising the Blue Betta 1 transformation, such cryopreserved testes deposited at the ATCC, to produce transgenic offspring. Such offspring may be, for example, a Betta, a species of the Betta splendens family, a fish species or genus related to Betta, or another fish species or genus. In some aspects, the fish may be produced using in vitro fertilization.

As used in this specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Any embodiment of any of the present methods, kits, and compositions may consist of or consist essentially of—rather than comprise/include/contain/have—the described features and/or steps. Thus, in any of the claims, the term "consisting of" or "consisting essentially of" may be substituted for any of the open-ended linking verbs recited above, in order to change the scope of a given claim from what it would otherwise be using the open-ended linking verb.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

Transgenic Fish

In some aspects, the present disclosure regards transgenic fish. Methods of making transgenic fish are described in, for example, U.S. Pat. Nos. 7,135,613; 7,700,825; 7,834,239, each of which is incorporated by reference in its entirety. For example, a transgenic green Betta may be generated using an expression cassette encoding green fluorescent protein (GFP), such as ZsGreen1. In another example, a transgenic orange Betta may be generated using an expression cassette encoding orange fluorescent protein (YFP), such as ZsYellow1. In another example, a transgenic red Betta may be generated using an expression cassette encoding red fluorescent protein (RFP), such as DsRed2. In another example, a transgenic purple Betta may be generated using an expression cassette encoding purple fluorescent protein (PFP), such as FP635. In another example, a transgenic blue Betta may be generated using an expression cassette encoding blue fluorescent protein (BFP), such as TagBFP, or TagBFP in combination with aeCP597.

It is preferred that fish belonging to species and varieties of fish of commercial value, particularly commercial value within the ornamental fish industry, be used. Such fish include but are not limited to bettas, catfish, zebrafish and other danios, medaka, carp, tilapia, goldfish, tetras, barbs, sharks (family cyprinidae, such as rainbow shark), angelfish, loach, koi, glassfish, discus, eel, goby, gourami, guppy, Xiphophorus, hatchet fish, Molly fish, or pangasius. A particular fish for use in the context of the present disclosure is a Betta. Bettas are increasingly popular ornamental animals and would be of added commercial value in various colors. Betta embryos are easily accessible and nearly transparent. Betta skin color is determined by pigment cells in the skin, which contain pigment granules called melanosomes. The number, size, and density of the melanosomes per pigment cell influence the color of the fish skin.

In commercial aquaculture, green Bettas are spawned naturally pairwise. A mature male is placed into a 1-3 gallon tanks and left overnight. If the male builds a bubble nest, a female is added and left overnight. After the spawning, the female is removed and the male is left in the tank to take care of the developing eggs. After three days, the male is removed and the fry are fed freshly hatched Artemia nauplii for 3-4 weeks, until the fry are large enough to be safely moved to a grow-out vat. It takes about three months for bettas to become mature.

Line Regeneration from cryopreserved testes

Gonad freezing methods are well-known in the art; see, e.g., Lee et al. (2013), and Seki et al. (2017), both of which are incorporated herein by reference in their entireties. To obtain the transgenic fish disclosed herein, germ cells obtained from dissociated frozen betta gonads may be used.

In an example embodiment, young adult male green bettas are euthanized using an overdose of sedative, such as Tricaine. The fish are decapitated, blotted dry, sprayed with 70% ethanol, dissected and their testes are removed and transferred into ice-cold L-15 medium. When the desired amount of tissue was obtained, the testes were transferred into ice-cold vitrification solution (L-15 medium containing 30% (v/v) of ethylene glycol, 21% (w/v) Ficoll PM-70, and 0.35M sucrose). After 20 minutes of incubation, testes were blotted to remove the vitrification solution and submerged into liquid nitrogen. The samples are kept in liquid nitrogen for long term storage.

To recover green betta line, the cryopreserved testes are thawed in 0.2M sucrose solution in L-15 medium at 25° C. for 5 seconds and incubated in the same solution for 5 minutes at 0° C. The thawed testes are transferred into L-15 medium containing 10% Fetal Bovine Serum (FBS), minced, transferred into L-15 medium containing 0.2% collagenase H, 0.15% dispase II, and 900 U/ml of DNase I and incubated for 1 hour at 25° C. with constant gentle agitation to dissociate the tissue into cells. The cell suspension is rinsed once with L-15 containing 10% FBS, and filtered through 60-micron mesh. The cell suspension is then injected into 7 day old betta fry anesthetized with Tricaine. The injected fry are reared to adulthood and spawned using regular protocol to obtain green betta progeny.

The present disclosure further encompasses progeny of a transgenic fish containing the Green Betta 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Green Betta 1 transformation event is by visual inspection, as the fish in question would be green colored and immediately distinguishable from non-transgenic fish.

In an example embodiment, young adult male orange bettas are euthanized using an overdose of sedative, such as Tricaine. The fish are decapitated, blotted dry, sprayed with 70% ethanol, dissected and their testes are removed and transferred into ice-cold L-15 medium. When the desired amount of tissue was obtained, the testes were transferred into ice-cold vitrification solution (L-15 medium containing 30% (v/v) of ethylene glycol, 21% (w/v) Ficoll PM-70, and 0.35M sucrose). After 20 minutes of incubation, testes were blotted to remove the vitrification solution and submerged into liquid nitrogen. The samples are kept in liquid nitrogen for long term storage.

To recover orange betta line, the cryopreserved testes are thawed in 0.2M sucrose solution in L-15 medium at 25° C. for 5 seconds and incubated in the same solution for 5 minutes at 0° C. The thawed testes are transferred into L-15 medium containing 10% Fetal Bovine Serum (FBS), minced, transferred into L-15 medium containing 0.2% collagenase H, 0.15% dispase II, and 900 U/ml of DNase I and incubated for 1 hour at 25° C. with constant gentle agitation to dissociate the tissue into cells. The cell suspension is rinsed once with L-15 containing 10% FBS, and filtered through 60-micron mesh. The cell suspension is then injected into 7 day old betta fry anesthetized with Tricaine. The injected fry are reared to adulthood and spawned using regular protocol to obtain orange betta progeny.

The present disclosure further encompasses progeny of a transgenic fish containing the Orange Betta 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Orange Betta 1 transformation event is by visual inspection, as the fish in question would be orange colored and immediately distinguishable from non-transgenic fish.

In an example embodiment, young adult male red bettas are euthanized using an overdose of sedative, such as Tricaine. The fish are decapitated, blotted dry, sprayed with 70% ethanol, dissected and their testes are removed and transferred into ice-cold L-15 medium. When the desired amount of tissue was obtained, the testes were transferred into ice-cold vitrification solution (L-15 medium containing 30% (v/v) of ethylene glycol, 21% (w/v) Ficoll PM-70, and 0.35M sucrose). After 20 minutes of incubation, testes were blotted to remove the vitrification solution and submerged into liquid nitrogen. The samples are kept in liquid nitrogen for long term storage.

To recover red betta line, the cryopreserved testes are thawed in 0.2M sucrose solution in L-15 medium at 25° C. for 5 seconds and incubated in the same solution for 5 minutes at 0° C. The thawed testes are transferred into L-15 medium containing 10% Fetal Bovine Serum (FBS), minced, transferred into L-15 medium containing 0.2% collagenase H, 0.15% dispase II, and 900 U/ml of DNase I and incubated for 1 hour at 25° C. with constant gentle agitation to dissociate the tissue into cells. The cell suspension is rinsed once with L-15 containing 10% FBS, and filtered through 60-micron mesh. The cell suspension is then injected into 7 day old betta fry anesthetized with Tricaine. The injected fry are reared to adulthood and spawned using regular protocol to obtain red betta progeny.

The present disclosure further encompasses progeny of a transgenic fish containing the Red Betta 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Red Betta 1 transformation event is by visual inspection, as the fish in question would be red colored and immediately distinguishable from non-transgenic fish. It should also be appreciated that depending on the specific RFP used and/or the insertion location of the expression cassette, the transgenic red Betta may have a color that fades over the course of the transgenic red Betta's life. For example, the red transgenic Betta may change in color from red to pale red, or from red to pink. In addition, depending on the specific RFP used and/or the insertion location of the expression cassette, the transgenic red Betta may have a color that fades over generations. For example, the red transgenic Betta may change in color from one generation to the next, such that an older generation may exhibit the red color, but a younger generation may appear pale red, or pink.

In an example embodiment, young adult male purple bettas are euthanized using an overdose of sedative, such as Tricaine. The fish are decapitated, blotted dry, sprayed with 70% ethanol, dissected and their testes are removed and transferred into ice-cold L-15 medium. When the desired amount of tissue was obtained, the testes were transferred into ice-cold vitrification solution (L-15 medium containing 30% (v/v) of ethylene glycol, 21% (w/v) Ficoll PM-70, and 0.35M sucrose). After 20 minutes of incubation, testes were blotted to remove the vitrification solution and submerged into liquid nitrogen. The samples are kept in liquid nitrogen for long term storage.

To recover purple betta line, the cryopreserved testes are thawed in 0.2M sucrose solution in L-15 medium at 25° C. for 5 seconds and incubated in the same solution for 5 minutes at 0° C. The thawed testes are transferred into L-15 medium containing 10% Fetal Bovine Serum (FBS), minced, transferred into L-15 medium containing 0.2% collagenase H, 0.15% dispase II, and 900 U/ml of DNase I and incubated for 1 hour at 25° C. with constant gentle agitation to dissociate the tissue into cells. The cell suspension is rinsed once with L-15 containing 10% FBS, and filtered through 60-micron mesh. The cell suspension is then injected into 7 day old betta fry anesthetized with Tricaine. The injected fry are reared to adulthood and spawned using regular protocol to obtain purple betta progeny.

The present disclosure further encompasses progeny of a transgenic fish containing the Purple Betta 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Purple Betta 1 transformation event is by visual inspection, as the fish in question would be purple colored and immediately distinguishable from non-transgenic fish.

In an example embodiment, young adult male blue bettas are euthanized using an overdose of sedative, such as Tricaine. The fish are decapitated, blotted dry, sprayed with 70% ethanol, dissected and their testes are removed and transferred into ice-cold L-15 medium. When the desired amount of tissue was obtained, the testes were transferred into ice-cold vitrification solution (L-15 medium containing 30% (v/v) of ethylene glycol, 21% (w/v) Ficoll PM-70, and 0.35M sucrose). After 20 minutes of incubation, testes were blotted to remove the vitrification solution and submerged into liquid nitrogen. The samples are kept in liquid nitrogen for long term storage.

To recover blue betta line, the cryopreserved testes are thawed in 0.2M sucrose solution in L-15 medium at 25° C. for 5 seconds and incubated in the same solution for 5 minutes at 0° C. The thawed testes are transferred into L-15 medium containing 10% Fetal Bovine Serum (FBS), minced, transferred into L-15 medium containing 0.2% collagenase H, 0.15% dispase II, and 900 U/ml of DNase I and incubated for 1 hour at 25° C. with constant gentle agitation to dissociate the tissue into cells. The cell suspension is rinsed once with L-15 containing 10% FBS, and filtered through 60-micron mesh. The cell suspension is then injected into 7 day old betta fry anesthetized with Tricaine. The injected fry are reared to adulthood and spawned using regular protocol to obtain blue betta progeny.

The present disclosure further encompasses progeny of a transgenic fish containing the Blue Betta 1 transformation event, as well as such transgenic fish derived from a transgenic fish egg, sperm cell, embryo, or other cell containing a genomically integrated transgenic construct. "Progeny," as the term is used herein, can result from breeding two transgenic fish of the invention, or from breeding a first transgenic fish of the invention to a second fish that is not a transgenic fish of the invention. In the latter case, the second fish can, for example, be a wild-type fish, a specialized strain of fish, a mutant fish, or another transgenic fish. The second fish may be of the same species, or may be of a different species or genus. The hybrid progeny of these matings have the benefits of the transgene for fluorescence combined with the benefits derived from these other lineages.

The simplest way to identify fish containing the Blue Betta 1 transformation event is by visual inspection, as the fish in question would be blue colored and immediately distinguishable from non-transgenic fish.

EXAMPLES

Certain embodiments of the invention are further described with reference to the following examples. These examples are intended to be merely illustrative of the invention and are not intended to limit or restrict the scope of the present invention in any way and should not be construed as providing conditions, parameters, reagents, or starting materials that must be utilized exclusively in order to practice the art of the present invention.

Example 1

Green Transgenic Betta

Transgenic fish exhibiting a green color are provided. The specific transgenic events embodied in these fish are designated the "Green Betta 1 transformation event". Germ cells from these fish may be implanted into Betta fry and thereby breed transgenic Betta that comprise these specific transgenic integration events. Cryopreserved testes from this line were deposited at the American Type Culture Collection, 10801 University Blvd, Patent Depository—P0072913, Manassas, Va. 20110-2209, under the provisions of the Budapest Treaty as "Green Betta 1" under Provisional Accession Number PTA-126548.

Example 2

Orange Transgenic Betta

Transgenic fish exhibiting an orange color are provided. The specific transgenic events embodied in these fish are designated the "Orange Betta 1 transformation event". Germ cells from these fish may be implanted into Betta fry and thereby breed transgenic Betta that comprise these specific transgenic integration events. Cryopreserved testes from this line were deposited at the American Type Culture Collection, 10801 University Blvd, Patent Depository—P0072913, Manassas, Va. 20110-2209, under the provisions of the Budapest Treaty as "Orange Betta 1" under Provisional Accession Number PTA-126549.

Example 3

Red and/or Pink Transgenic Betta

Transgenic fish exhibiting a red color are provided. The specific transgenic events embodied in these fish are designated the "Red Betta 1 transformation event". Germ cells from these fish may be implanted into Betta fry and thereby breed transgenic Betta that comprise these specific transgenic integration events. Cryopreserved testes from this line were deposited at the American Type Culture Collection, 10801 University Blvd, Patent Depository—P0072913, Manassas, Va. 20110-2209, under the provisions of the Budapest Treaty as "Pink Betta PiBS2019" under Provisional Accession Number PTA-126550.

Example 4

Purple Transgenic Betta

Transgenic fish exhibiting a purple color are provided. The specific transgenic events embodied in these fish are designated the "Purple Betta 1 transformation event". Germ cells from these fish may be implanted into Betta fry and thereby breed transgenic Betta that comprise these specific transgenic integration events. Cryopreserved testes from this line were deposited at the American Type Culture Collection, 10801 University Blvd, Patent Depository—P0072913, Manassas, Va. 20110-2209, under the provisions of the Budapest Treaty as "Purple Betta 1".

Example 5

Blue Transgenic Betta

Transgenic fish exhibiting a blue color are provided. The specific transgenic events embodied in these fish are designated the "Blue Betta 1 transformation event". Germ cells from these fish may be implanted into Betta fry and thereby breed transgenic Betta that comprise these specific transgenic integration events. Cryopreserved testes from this line were deposited at the American Type Culture Collection, 10801 University Blvd, Patent Depository—P0072913, Manassas, Va. 20110-2209, under the provisions of the Budapest Treaty as "Blue Betta 1".

The fluorescent transgenic fish have use as ornamental fish in the market. Stably expressing transgenic lines can be developed by breeding a transgenic individual with a wild-type fish, mutant fish, or another transgenic fish. The desired transgenic fish can be distinguished from non-transgenic fish by observing the fish in white light, sunlight, ultraviolet light, blue light, or any other useful lighting condition that allows visualization of the green, orange, red, pink, purple or blue color of the transgenic fish.

The fluorescent transgenic fish should also be valuable in the market for scientific research tools because they can be used for embryonic studies such as tracing cell lineage and cell migration. Additionally, these fish can be used to mark cells in genetic mosaic experiments and in fish cancer models.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A transgenic Betta comprising a chromosomally integrated expression cassette encoding a green, red or orange fluorescent protein, wherein the Betta comprises a transformation event from sperm selected from a group consisting of a "Green Betta 1 transformation event", an "Orange Betta 1 transformation event and a "Red Betta 1 transformation event", sperm exhibiting the Green Betta 1 transformation event having been deposited at the ATCC as deposit number PTA-126548, sperm exhibiting the Orange Betta 1 transformation event having been deposited at the ATCC as deposit number PTA-126549, and sperm exhibiting the Red Betta 1 transformation event having been deposited at the ATCC as deposit number PTA-126550.

2. The transgenic Betta of claim 1, further defined as a fertile, transgenic Betta.

3. The transgenic Betta of claim 1, wherein the fish is homozygous for the integrated expression cassette.

4. The transgenic Betta of claim 1, wherein the fish is heterozygous for the integrated expression cassette.

5. A method of providing a transgenic Betta to the ornamental fish market, comprising obtaining a transgenic Betta in accordance with claim 1, and distributing the fish to the ornamental fish market.

6. The method of claim 5, wherein the fish are distributed by a grower to a commercial distributor.

7. The method of claim 5, wherein the fish are distributed by a grower or a commercial distributor to a retailer.

8. The method of claim 7, wherein the retailer is a multi-product retailer having an ornamental fish department.

9. A method of producing a transgenic Betta comprising: (a) obtaining a Betta that comprises a chromosomally integrated expression cassette encoding a green, red or orange fluorescent protein in accordance with claim 1; and (b) breeding the obtained Betta with a second Betta to provide a transgenic Betta, wherein the transgenic Betta comprises the transformation event.

10. The method of claim 9, wherein the second Betta is a non-transgenic Betta.

11. A progeny of a transgenic Betta of claim 1 that comprises a chromosomally integrated expression cassette encoding a fluorescent protein, wherein the progeny Betta comprises a transformation event selected from a group consisting of a "Green Betta 1 transformation event", an "Orange Betta 1 transformation event", a "Red Betta 1 transformation event",.

12. The progeny fish of claim 11, further defined as a fertile, transgenic Betta.

13. The progeny fish of claim 11, wherein the progeny Betta is homozygous for the integrated expression cassette.

14. The progeny fish of claim 11, wherein the progeny Betta is heterozygous for the integrated expression cassette.

15. A method of providing a transgenic fish to the ornamental fish market, comprising obtaining a progeny fish in accordance with claim 11, and distributing the fish to the ornamental fish market.

16. The method of claim 15, wherein the fish are distributed by a grower to a commercial distributor.

17. The method of claim 16, wherein the fish are distributed by a grower or a commercial distributor to a retailer.

18. The method of claim 17, wherein the retailer is a multi-product retailer having an ornamental fish department.

19. A method of producing a transgenic fish comprising: (a) obtaining a transgenic fish in accordance with claim 11; and (b) breeding the obtained fish with a second fish to provide a transgenic fish comprising the transformation event.

20. The method of claim 19, wherein the second fish is a non-transgenic fish.

21. Cell lines for making a transgenic Betta comprising: cells comprising the Green Betta 1 transformation event deposited at the ATCC as deposit number PTA-126548, cells comprising the Orange Betta 1 transformation event deposited at the ATCC as deposit number PTA-126549, and cells comprising the Red Betta 1 transformation event deposited at the ATCC as deposit number PTA-126550.

* * * * *